US00PP32380P2

(12) United States Plant Patent
Hansen

(10) Patent No.: US PP32,380 P2
(45) Date of Patent: Oct. 20, 2020

(54) ***DICENTRA* PLANT NAMED 'PINK DIAMONDS'**

(50) Latin Name: *Dicentra*
Varietal Denomination: Pink Diamonds

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/602,617

(22) Filed: Nov. 8, 2019

(51) Int. Cl.
*A01H 5/02* (2018.01)
*A01H 6/64* (2018.01)

(52) U.S. Cl.
USPC ..... Plt./426
CPC ..... *A01H 6/64* (2018.05)

(58) Field of Classification Search
USPC ..... Plt./426
CPC ..... A01H 6/64; A01H 5/02
See application file for complete search history.

*Primary Examiner* — Keith O. Robinson

(57) ABSTRACT

A new and unique Fern-leafed Bleeding Heart, *Dicentra* plant named 'Pink Diamonds' characterized by compact habit and fern-like blue-green foliage. The plant flowers with two-tone pink and white heart-shaped lightly-fragrant flowers on panicles that have extended flowering periods on older panicles and new with panicles to stay in bloom 16 to 20 weeks beginning late spring. The new plant has an excellent growth rate.

2 Drawing Sheets

Botanical classification: *Dicentra*.
Variety denomination: 'Pink Diamonds'.

STATEMENT REGARDING PRIOR DISCLOSURES UNDER 37 CFR 1.77(B)(6)

The first non-enabling disclosure of the claimed plant, in the form of a calendar photograph, was made by Walters Gardens, Inc. on Nov. 20, 2018. Since this disclosure the plant was also featured with a photo and brief description on Dec. 1, 2018 on a website maintained by Walters Gardens, Inc. and in the Walters Gardens 19-20 Catalog on May 29, 2019. Plants for these photograph and information were obtained from the inventor. No plants of *Dicentra* 'Pink Diamonds' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct *Dicentra* 'Pink Diamonds' hereinafter referred to also by the cultivar name 'Pink Diamonds' and the new plant. 'Pink Diamonds' is the result of a self-pollination of *Dicentra* 'Firecracker' (not patented) on Jun. 10, 2015 at a private garden in Zeeland, Mich., USA. Through trials at a wholesale perennial nursery the plant was referred to by the code 15-1-1. The new plant has been successfully asexually propagated initially by division in 2017 followed by shoot tip tissue culture at the same nursery in Zeeland, Mich. Both these asexual propagation systems has been found to produce stable and identical plants that maintain all the unique characteristics of the original plant in successive generations.

BRIEF DESCRIPTION OF THE INVENTION

The new plant can be most closely compared with: 'Amore Pink' U.S. Plant Pat. No. 25,601, 'Amore Rose' U.S.

Plant Pat. No. 25,623, 'Candy Hearts' U.S. Plant Pat. No. 14,692, 'Firecracker' and 'Fire Island' U.S. Plant Pat. No. 22,488. 'Amore Pink' has deeper pink flower color without the white of the recurved petals and more open habit and less dense. 'Amore Rose' has darker reddish flowers and less dense and more open habit. 'Candy Hearts' has deeper pink flower color without the white of the recurved petals. 'Firecracker' has much deeper reddish flower color without the white of the recurved petals. 'Fire Island' has a darker purplish red coloration, is less vigorous in growth, is less tolerant of higher temperatures, is shorter in habit and has a shorter flowering season.

The new plant, 'Pink Diamonds', is unique from all Fern-leaf Bleeding Hearts known to the inventor by the following combined traits:

1. Compact habit of finely-textured, fern-like blue-green foliage;
2. Pink buds open to two-tone, heart-shaped, lightly-fragrant flowers;
3. Repeat flowering panicles and extended flowering on older panicles;
4. Flowering beginning in late spring and continuing for 16 to 20 weeks.

BRIEF DESCRIPTION OF THE DRAWINGS

The color drawings illustrate the overall characteristics of the new plant and demonstrates the overall appearance of the new plant including the unique traits as a three-year-old plant growing in a full-sun trial garden in Zeeland, Mich. with supplemental water and fertilizer as needed. The colors are as true as reasonably possible given the technology available. The colors are as accurate as reasonably given the technology available. The colors are as accurate as reasonably possible with color reproductions. Ambient light, spectrum, temperature, source, duration and direction may cause minor variation in appearance.

DETAILED DESCRIPTION OF THE INVENTION

Figure 1:
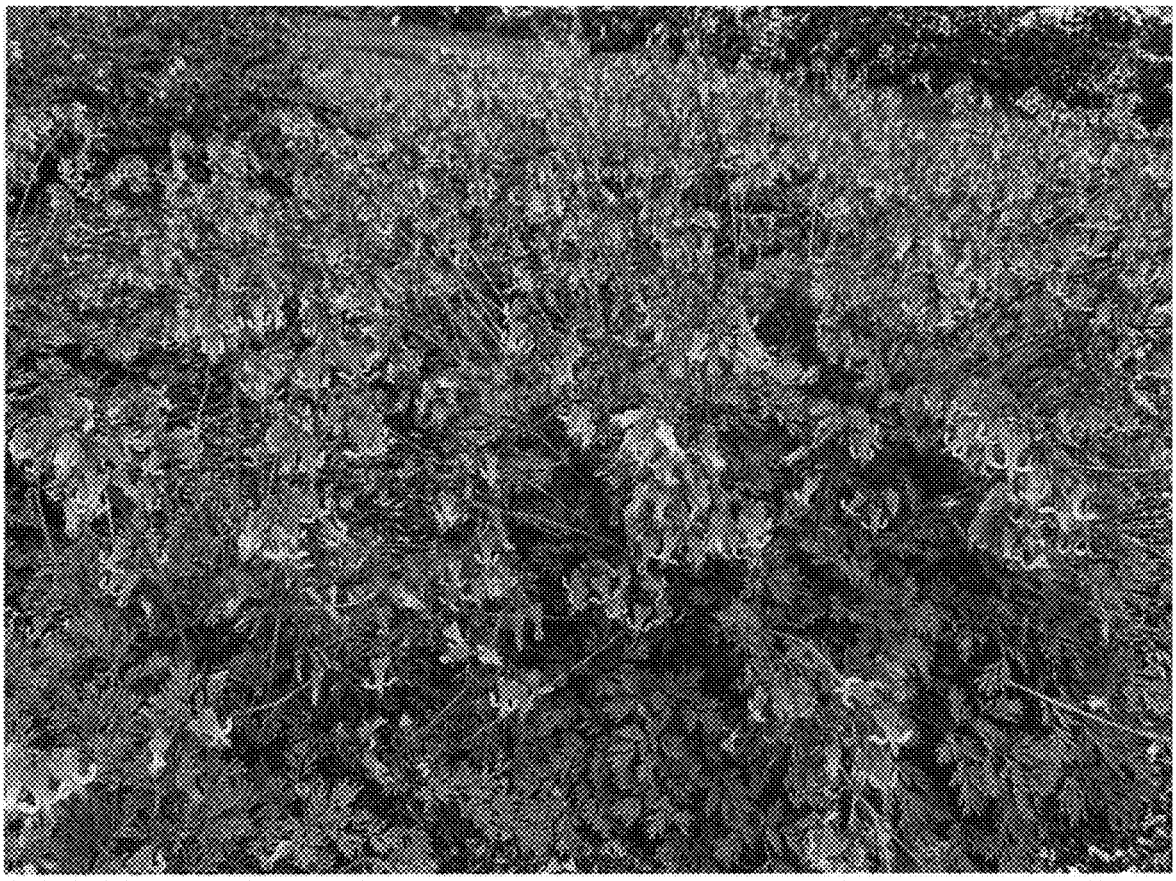
FIG. 1 shows the new plant grown in a full-sun trial garden.
Figure 2:
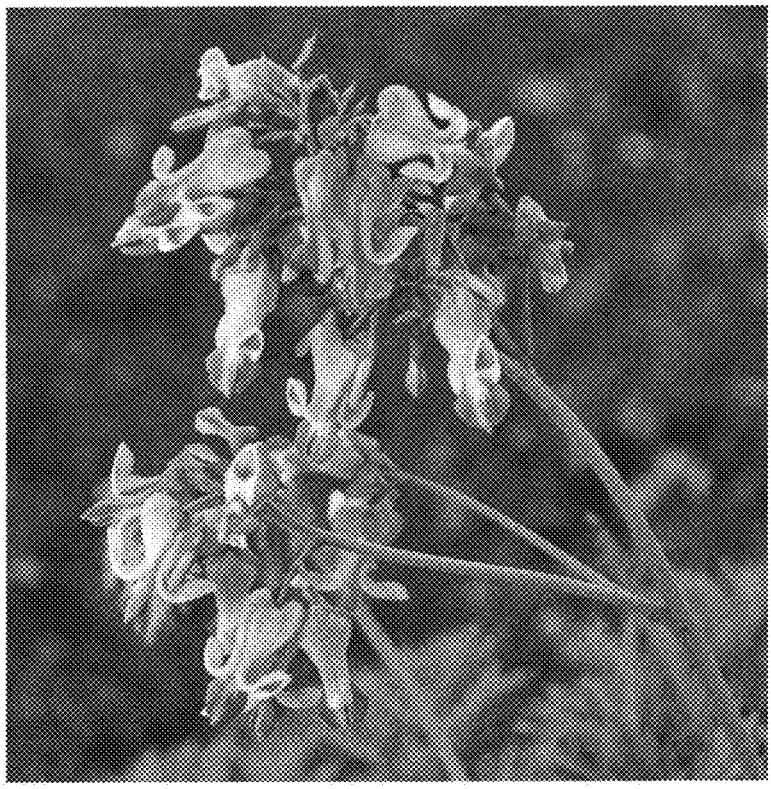
FIG. 2 shows close-up of the top of a young flower panicle.
Figure 3:
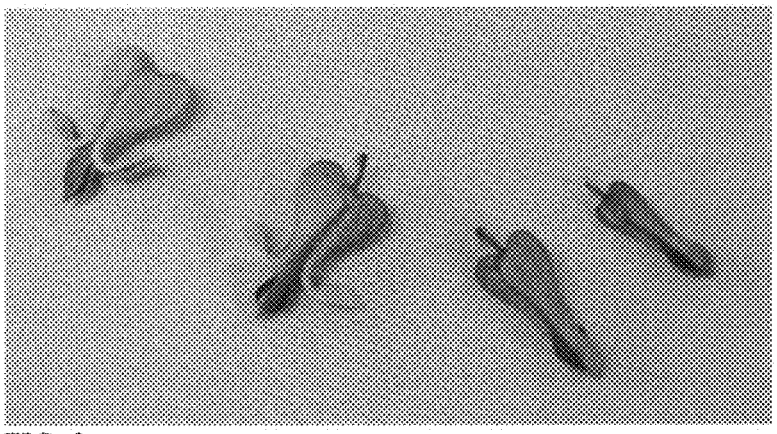
FIG. 3 shows a close-up of the flowers and buds in decreasing maturity from left to right.

The following detailed description is based on a three-year-old plant growing in a full-sun trial garden in Zeeland, Mich., USA. Environmental conditions for the growing season daytime temperatures range between 12-30° C., and night temperatures range between 6-19° C. Except for ordinary dictionary color usage, color references are according to The Royal Horticultural Society Colour Chart, 2015 edition.

Parentage: Female or seed parent is 'Firecracker'; male or pollen parent is 'Firecracker';

Asexual propagation: Plant tissue culture, time to finish from a 25 mm plug to a 3.8 liter container about 10 to 12 weeks;

Plant habit: Herbaceous, winter-hardy perennial; forming compact mound with about 20 underground divisions;

Size: Foliage grows to 24 cm tall to top of foliage and 52 cm wide.

Vigor: Excellent; growing best in well-drained soil in full-sun;

Leaf: Triternate; dissected; deltoid in outline; to 12.5 cm long and 15.0 cm wide; glabrous adaxial and abaxial;

Lobes: To 7.5 cm long and 7.0 cm wide; each main lobe further sectioned into three with side lobes divided into three segments with up to 50 smaller divisions of lobes and terminal section divided into up to 52 divisions; secondary lobes to 11.0 cm wide and 7.0 cm long; individual lobes to about 2.5 mm across and 10.0 mm long; individual lobe apices acute, margin entire;

Leaf color: Emerging and developing adaxial nearest blend of RHS 188C and RHS N138D, emerging and developing abaxial nearest blend of RHS 188D and RHS N138D; mature adaxial nearest RHS 139A and RHS 189B, mature abaxial nearest RHS N138D and RHS 188C;

Venation: Pinnate;

Vein color: Same as surrounding tissue;

Petiole: Cylindrical; flexible; to 18.5 cm long and 2.0 mm diameter above clasping base, base to about 6.0 mm across;

Petiole color: Distally near lobe stems nearest RHS 146D, proximally nearest RHS 160D with spotting increasing proximally nearest RHS 183C;

Inflorescence: Paniculate; about 110 per plant; flowering in upper 9.0 cm to 6.0 cm across; between 10 to 42 flowers open at one time per stem; with new inflorescences beginning throughout flowering season;

Number of flowers: About 10 to 143 per panicle, increasing as season progresses;

Peduncle: Cylindrical; glabrous; to 38.0 cm long and 4.5 mm diameter; color proximally nearest RHS 146D, distally becoming maculate with RHS N77B;

Pedicel: Cylindrical; glabrous; slightly glaucous; to 7.0 mm long and about 0.7 mm diameter; color N138D;

Flower bud: One day prior to opening inverted vase-shaped, narrowest in middle; base cordate; apex acute; to about 20.0 mm long, 10.0 mm wide and 7.0 mm thick at the base, about 3.0 mm diameter in middle and near apex 5.0 mm across with wings extending to about 7.0 mm across; five days from opening to about 18.0 mm long and 6.0 mm wide and 3.5 mm thick at the base, 2.5 mm diameter in middle and near apex about 4.0 mm across with wings extending to about 4.0 mm across;

Flower season: Beginning week 18 and continuing for about 16 weeks;

Flower lastingness: Individually about one week; each scape about 4 to 6 weeks;

Bud color: One day prior to opening proximally nearest RHS N66D on narrow side and lighter than RHS N66D on broader side; distally nearest RHS 155C with apex nearest RHS 158B; distal protruding wing nearest RHS 72B; five days from opening proximally nearest RHS 60C; distally between RHS 145C and RHS 145D, distal protruding wing nearest RHS N66D;

Flower: Zygomorphic; proximally cordate; laterally slightly applanate; with two sets of petals; about 21.0 mm long, 11.0 mm wide at base, 4.0 mm wide at constriction, 18.0 mm wide at reflexed outer petal apices, 3.5 mm wide near inner petal apex; base 7.5 mm thick;

Corolla: Outer petals opposite, inflated proximally, concavo-convex and reflexed distally; glabrous, fleshy and stiff; apex acute; basal 2.0 mm fused; margin entire; to 21.0 mm long extended and 16.0 mm long in reflexed state, 7.0 mm wide near base and 3.5 mm wide from constriction to near apex; outer petal color abaxial base nearest RHS N66D lightening to between RHS 73C and RHS 73D with veins of nearest RHS 73A and finally before dropping nearest RHS 76D; abaxial apex nearest RHS N155D; adaxial base nearest RHS 69B, maculate increasing toward center with RHS 61A, distally with two water-marks nearest RHS 79D on background nearest RHS NN155C with terminal 0.5 mm of apex nearest RHS NN155A; inner petals opposite, at right angle to outer set; spatulate with distal portion fleshy and cupped; apex fused in distal 1.0 mm; about 17.0 mm long and 4.0 mm wide in distal portion, 2.0 mm wide in basal 11.0 mm; with keeled, central, abaxial wing in distal 5.0 mm extending about 2.0 mm; inner petal color adaxial cupped portion nearest RHS N79A, proximally nearest RHS NN155D finely maculate with nearest RHS 71A; abaxial wing nearest RHS N79B, distal margins nearest N79A and distal centers nearest RHS NN155D, basal 11.0 mm nearest blend between RHS 65D and RHS 67C with midrib of nearest RHS N80B;

Sepals: 2; deltoid; opposite; adpressed to corolla; acute apex; truncate base; margin entire; glabrous adaxial and abaxial; hyaline; 5.0 mm long and 4.0 mm wide; color nearest RHS 155B maculate with increasing density proximally with nearest RHS 60C;

Gynoecium: Single; 16.0 mm long; erect, straight;

Style: About 8.0 mm long and 1.0 mm diameter at ovary, tapering toward stigma; color nearest RHS N144D;

Stigma: With two apices about 1.0 mm long protruding from a base about 1.5 mm across and 1.0 mm thick; color nearest RHS NN155A;

Ovary: Oblong; fusiform, tapering toward style and base; apex acute; base truncate; 7.0 mm long and 2.0 mm diameter near middle; color nearest RHS 146A;

Androecium: Six; anthers and distal one-half of filaments connate into two groups;

Filaments: Petaloid; in two groups at right angle to inner petal; fused near apical 5.0 mm, free in distal 2.0 mm;

bases separate; two lateral and one central in each group; two lateral filaments to about 2.0 mm wide near base and about 15.0 mm long, central filament to about 1.0 mm wide near base and about 18.0 mm long, tapering to about 0.2 mm diameter in distal 2.0 mm; color basally nearest blend of RHS 65D and RHS 69D with midrib extending to near longitudinal center of nearest RHS 65C; distal 2.0 mm white nearest RHS NN155D;

Anthers: Closely arranged just below stigma; ellipsoidal; about 2.0 mm long and 0.7 mm across; color nearest RHS 4A;

Pollen: Abundant; color nearest RHS 12A;

Fragrance: Lightly sweet;

Fruit and seed: No fruit or seed observed to date;

Pest and disease tolerance: 'Pink Diamonds' has not shown susceptibility to insects of the sub-families *Aphidoidea* and *Alevrodoidea* or fungi of unknown scientific names that are frequent pests and diseases of other cultivars in the genus *Dicentra.*

I claim:

1. A new and distinct cultivar of Fern-leafed Bleeding Heart, *Dicentra* plant named 'Pink Diamonds' as herein described and illustrated.

* * * * *